United States Patent [19]
Amick et al.

[11] Patent Number: 5,868,879
[45] Date of Patent: Feb. 9, 1999

[54] COMPOSITE ARTICLE, ALLOY AND METHOD

[75] Inventors: Darryl Dean Amick, Albany; John C. Haygarth, Corvallis; Hershel R. Henson, Albany, all of Oreg.

[73] Assignee: Teledyne Industries, Inc., Albany, Oreg.

[21] Appl. No.: 654,000

[22] Filed: May 28, 1996

Related U.S. Application Data

[63] Continuation of Ser. No. 214,223, Mar. 17, 1994, abandoned.

[51] Int. Cl.$^6$ .............................. A61F 2/02; C22C 14/00
[52] U.S. Cl. ..................... 148/669; 420/417; 420/420; 148/421; 501/103
[58] Field of Search .................... 148/669, 421; 420/417, 420; 501/103

[56] References Cited

U.S. PATENT DOCUMENTS

| | | | |
|---|---|---|---|
| 2,892,706 | 6/1959 | Jaffee | 75/175.5 |
| 2,987,352 | 6/1961 | Watson | 308/241 |
| 3,370,946 | 2/1968 | Bertea | 75/175.5 |
| 3,643,658 | 2/1972 | Steinemann et al. | 128/92 |
| 3,677,795 | 7/1972 | Bokros | 117/46 |
| 3,752,664 | 8/1973 | Steinemann et al. | 75/134 |
| 3,777,346 | 12/1973 | Steinemann | 29/180 |
| 3,849,124 | 11/1974 | Villani | 75/177 |
| 3,911,783 | 10/1975 | Gapp et al. | 85/73 |
| 4,040,129 | 8/1977 | Steinemann et al. | 1/24 |
| 4,145,764 | 3/1979 | Suzuki et al. | 3/1.9 |
| 4,170,990 | 10/1979 | Baumgart et al. | 128/92 |
| 4,197,643 | 4/1980 | Burstone et al. | 7/58 |
| 4,511,411 | 4/1985 | Brunner et al. | 148/20.3 |
| 4,857,269 | 8/1989 | Wang et al. | 420/417 |
| 4,902,359 | 2/1990 | Takeuchi et al. | |
| 5,372,660 | 12/1994 | Davidson et al. | 148/669 |
| 5,415,704 | 5/1995 | Davidson | 148/316 |

FOREIGN PATENT DOCUMENTS 2703529  8/1978  Germany.

OTHER PUBLICATIONS

Brown & Merritt, Evaluation of Corrosion Resistance of Biology; Case Western Reserve University, 13 Feb. 1986 (1:8).
Mears, "Electron—Probe Microanalysis of Tissue & Cells from Iny/Ant Areas", Jnl of Bone & Joint Surgery, vol. 48B, No. 3, pp. 567–576 (Aug. 1966).
Ferguson, Laing & Hodge, "The Ionization of Metal Implants in Living Tissues" Jnl of Bone & Joint Surgery, vol. 42A, No. 1, pp. 77–90 (Jan. 1960).
Jepson et al in The Science & Tech . . . Titanium ed. Jaffee et al, Pergamon, N.Y, 1968, p. 677.
Heller et al Jour. Less–Common Metch, 24 (1971) 265.
Van Noort, R. Jour. Mat. Sci. 22 (1987) 3801.
Hoar and Mears, "Corrosion–Resistant Alloys in Chloride Solutions: Materials for Surgical Implants" pp. 506–507.
Kirk–Othmer Encyclopedia of Chemical Technology, vol. 23 pp. 98–113.
Collins, "Physical Metallurgy of Titanium Alloys", American Society for Metals Series in Metal Processing.
Zwicker et al Z. Metallkunde, 61 (1970) pp. 836–847.
Collins (ed) A Sourcebook of Titanium Alloy Superconductivity, Plenum, NY 1983 pp. 342, 352, 357, 358, 366, 405–419.
Albert, et al Z Metallkde, 63 (1972) 126.

*Primary Examiner*—Sam Silverberg
*Attorney, Agent, or Firm*—Shoemaker & Mattare,Ltd.

[57] ABSTRACT

A mixed oxide ceramic product is made directly from a metal alloy of titanium, zirconium and/or hafnium and niobium, tantalum or hafnium, where the normally combustible alloy of titanium and zirconium or hafnium is passivated by the addition of more than about 7 atomic percent of niobium and/or tantalum and or vanadium which alloy can then be heated in air at atmospheric pressure to a temperature of from about 800 degrees C. to about 1500 degrees C. to produce an adherent monolithic ceramic containing product.

4 Claims, 14 Drawing Sheets

TERNARY OXIDATION DIAGRAM
FOR Ti-Zr-Nb ALLOYS AT 700°C

OXIDATION OF Ti RICH Ti-Zr-Nb
ALLOYS AT 700°C

TERNARY OXIDATION DIAGRAM
FOR Ti-Zr-Nb ALLOYS AT 700°C

# COMPOSITE ARTICLE, ALLOY AND METHOD

This application is a Continuation of application Ser. No. 08/214,223, filed Mar. 17, 1994, now abandoned.

FIELD OF THE INVENTION

The present invention relates to the manufacture of ceramic layers on metal, shaped ceramic bodies, cermet articles, composite articles, and alloys used in such manufacture and more particularly to the field of reaction formed ceramics, articles made thereby, and alloys for use in their manufacture.

BACKGROUND OF THE INVENTION

Many of the alloys of titanium with zirconium or hafnium are characterized by their extraordinarily rapid oxidation in air at only modestly elevated temperatures. This characteristic has severely limited the usefulness of such alloys for many applications that could otherwise advantageously use the other physical properties of those alloys. In particular, the light weight, high strength and corrosion resistance of the alloys, as well as their electrical conductivity properties, biocompatibility, ease of closed-die forming and other desirable properties have not been fully exploited due to the potential ignition of the alloy in air at relatively low temperatures.

OBJECTS OF THE INVENTION

It is therefore an object of the present invention to provide utility to a class of titanium and zirconium alloys. It is a further object of the present invention to provide a method of fabricating a class of reaction formed ceramics directly formed from such alloys and articles produced thereby. It is yet a further object of the present invention to provide a method for forming adherent surfaces on such metal alloys which are hard, smoother, substantially inert and suitable for a wide variety of applications from cuttlery to implantable prosthetic devices, and method for renewing such monolithic surfaces.

SUMMARY OF THE INVENTION

Figure 1:
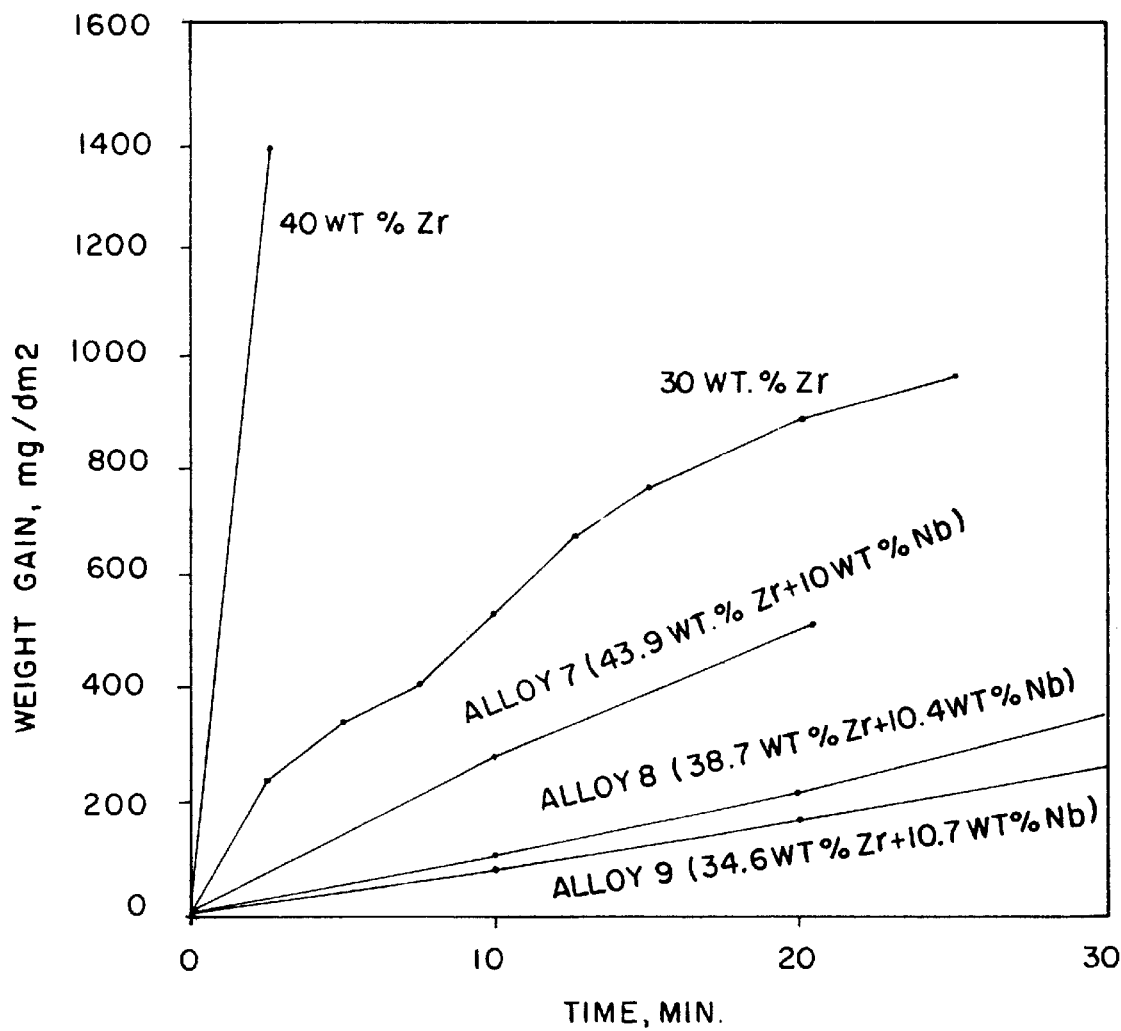
FIG. 1 is a graphical representation of some of the results reported in Table III of the weight gain of particular alloys at 700° C. as a function of time.

The inventors have discovered that ceramic bodies and a variety of ceramic surface layers formed in a metal body can be achieved by providing a substrate comprised of an alloy containing titanium, zirconium, and/or hafnium together with metals in minor amounts selected from the group consisting of niobium, tantalum and vanadium. The oxides of the metals can be obtained in situ by the controlled oxidation of the surface of the metal alloy substrate. Further, the present invention is particularly effective where the titanium and zirconium alloy is passivated against rapid oxidation by the presence of minor amounts of niobium or tantalum. Still further, oxides containing the metals of the metal alloys selected can be reaction formed throughout the metal alloy structure to reaction form either a monolithic cermet or ceramic body or structure by the selection of appropriate oxidation conditions.

DETAILED DESCRIPTION OF THE INVENTION

As used in this specification and the appended claims, the terms below are defined as follows:

"Ceramic" is not to be construed as being limited to a ceramic material in the classical sense, that is, in the sense that it consists entirely of non-metallic and inorganic materials, but rather refers to a material which is predominantly ceramic with respect to either composition or dominant properties, although the material may contain minor or substantial amounts of one or more metallic constituents.

"Microporosity": Porosity in which pore diameters are of the order of 1–10 $\mu$m ("microns"), as opposed to "macroporosity" in which pores are considerably larger than 10 $\mu$m.

"Oxidation reaction product" generally means one or more metals in an oxidized state wherein a metal has given up electrons to or shared electrons with another element, compound or combination thereof. Accordingly, an "oxidation reaction product" under this definition includes the product of the reaction of one or more metals with an oxidant, such as those described in this application.

"Oxidant" means one or more suitable electron acceptors or electron sharers which may be a solid, a liquid or a gas or some combination of these at the process conditions.

"Parent metal" is intended to refer to relatively pure metals, commercially available metals with impurities and/or alloying constituents therein, and alloys and intermetallic compounds of the metals. When a specific metal is mentioned, the metal identified should be read with this definition in mind unless indicated otherwise by the context.

A solid, liquid or vapor-phase oxidant, or a combination of such oxidants may be used, as noted hereinafter. For example, oxidants which may be emphasized include, without limitation, oxygen, nitrogen, ammonia, a halogen, sulphur, phosphorus, arsenic, carbon, boron, selenium, tellurium, and compounds and combinations thereof, for example, silica (as a source of oxygen), methane, ethane, propane, acetylene, ethylene, and propylene (as a source of carbon), and mixtures such as air, cracked ammonia, $N_2/H_2$, $H_2/CH_4$ and other hydrocarbons $H_2/H_2O$ and $CO/CO_2$, the latter two (i.e. $H_2/H_2O$ and $CO/CO_2$) being useful in reducing the oxygen activity of the environment.

A vapor-phase (gas) oxidant is preferred, and specific embodiments of the invention are described herein with reference to the use of vapor-phase oxidants. If a gas or vapor oxidant is used, the term "vapor-phase oxidant" means a vaporized or normally gaseous material which provides an oxidizing atmosphere. For example, oxygen or gas mixtures containing oxygen, including air, are preferred for obvious reasons of economy. When an oxidant is identified as containing or comprising a particular gas or vapor, this means an oxidant in which the identified gas or vapor is the sole oxidizer of the parent metal at certain conditions under the conditions employed in the oxidizing environment utilized. For example, although the major constituent of air is nitrogen, the oxygen content of air is the oxidizer for the parent metal because oxygen is a significantly stronger oxidant than nitrogen. Air therefore falls within the definition of an "oxygen-containing gas" oxidant but not normally within the definition of a "nitrogen-containing gas" oxidant.

In its preferred practice, the present invention will be described hereinafter with respect to alloys of titanium, zirconium or hafnium, or mixtures of the latter to which have been added minor amounts of other specific metals in sufficient quantity to render the overall alloy more resistant to rapid, combustion-like, oxidation at the temperatures described. It should be appreciated that wide composition limits are possible in the practice of the present invention when oxidation conditions are sufficiently controlled in any manner to prevent rapid reaction. For example, uncontrolled oxidation can be prevented where an inert gas diluent or reducing gas diluent is employed in a sufficient amount to prevent uncontrolled oxidation, or where the surface of the alloy is protected against unmoderated exposure to high concentrations of a gaseous oxidant. To obtain particularly advantageous metallurgical properties it may be necessary to conduct the oxidation reaction in air at elevated temperatures i.e., where combustion would normally occur. It may therefore be necessary to passivate the alloy of titanium, containing zirconium or hafnium, or mixture thereof, with minor amounts of a passivating metal or metal alloy, selected from the group consisting of niobium, tantalum or vanadium or mixture thereof. The foregoing also contemplates utilizing overpressures of oxygen where the Ti alloy has been passivated with niobium, tantalum or vanadium.

As will be more fully described hereinafter, the titanium alloys described herein and the process of their conversion into oxides or oxidation reaction products can be regulated to produce a type of cermet or ceramic product which product differs radically from prior attempts to provide inert wear resistant surfaces or cermet or ceramic bodies by either the bonding of inorganic ceramic-like material to the surface of a metal or by surface passivation reactions with molten salts or the like; or by the reaction formation of a ceramic body by the oxidation of a molten metal either alone or by infiltrating a preform matrix with an oxidizable metal and forming the ceramic in situ.

Typically, a rapid combustion-like reaction in air of some of the alloys described herein will produce a loose powder containing the single or mixed oxides of the parent metal and the alloy constituents. Such a result is, of course, unsatisfactory for the production of ceramic articles without further ceramic fabrication processing steps. The controlled oxidation of the present invention, directly produces unitary, monolithic adherent structural layers or rigid ceramic or cermet bodies. The processes of the present invention are suitable for the formation of shaped ceramic articles ceramic-metal composites and for the formation of smooth-hard impact resistant ceramic surfaces on metal articles. The present invention also contemplates the use of the alloys described as reinforcements in other ceramic articles which can be converted at high temperatures to the ceramic articles described herein in another ceramic body.

The present invention in its preferred practice forms oxide layers on the surface of the passivated alloys described, in air at temperatures of from about 300° C. to 800° C. and most preferably from about 500° C. to about 800° C. which layers are adherent, monolithic, hard, smooth, wear resistant surface layers. Moreover, since intricate shapes can be fabricated from the preferred metal alloy, the complete conversion of the alloy to oxides or mixed oxides can be controllably managed, preferably at temperatures of about 800° C. to about 1500° C. and for a sufficient period of time to produce shaped ceramic articles which have been substantially completely oxidized and typically contains uniformly distributed micro-porosity which varies in pore size when the process is conducted at different temperatures on the same starting material.

Due to the moderation of the rate of oxidation imparted by the processes and compositions described herein, relatively thick oxide layers can be obtained on the parent metal or metal alloy at moderate temperatures and within relatively short times. This is shown most clearly in FIGS. 6–8. It is therefore now feasible to provide a hard surface on the parent metal while retaining the strength or toughness of the underlying metal substrate. For example, surface oxide thicknesses of 2.5 to 25 $\mu$m can impart a hardness of approximately $R_c$ 70 to the cutting edge of a cutlery implement made from a titanium alloy comprising 35 wt. % zirconium and 10 wt. % niobium with the balance being titanium, by heating the implement in air at between about 300° C. to about 800° C. for a sufficient period of time to achieve the described hard, smooth oxide or ceramic layer. The process can even be repeated on a worn implement where a new hardened surface is desired using such readily available equipment as a conventional self-cleaning oven which is capable of reaching temperatures of about 300° C.

The utility of the present invention is further enhanced for many end use applications due to the excellent fabricability of the described titanium alloys. A wide range of mechanical properties is obtainable. Normally a titanium alloy containing 35 wt. % zirconium and 10 wt. % niobium exhibits a yield strength of only 2,000–3,000 psi at 1,350° F. (with 200% elongation). Such an alloy can however be solution-treated, quenched and aged to obtain a room temperature yield strength of 140,000 psi. The alloy can be closed-die-forged to obtain articles of complex shape which can subsequently be surface hardened by the controlled oxidation process described herein while retaining some of the mechanical properties imparted by the foregoing mill practice. The article can of course be completely oxidized to produce a monolithic ceramic body as previously discussed. Likewise, it is possible to investment cast the alloy to achieve the desired shape and subsequently oxidize the shaped article in a partial or complete manner as described. In this manner, cutlery implements, dental castings, orthopedic prosthetic devices and the like can be fabricated. Small parts requiring great wear resistance, such as is necessary in certain firearms mechanisms can particularly benefit from the practice of this invention.

An unexpected benefit is obtained by the practice of the present invention when making medical devices that in use are designed to bear against a plastic element, such as ultra high molecular weight polyethylene. The surface of the shaped article, after the controlled oxidation described herein to produce a smooth surface layer, is smooth enough to reduce attrition of the plastic or fretting of the plastic into small particles which is an undesirable phenomenon in some orthopedic prothesises implants. This advantage combined with the excellent biocompatibility of titanium-zirconium alloys and the possibility of forming materials having a generally low modulus of elasticity makes and the articles formed as described, highly desirable for such medial devices and in particular prosthetic devices. A low modulus better matches materials of relatively low stiffness such as mammalian bone. Likewise, the volume change upon conversion to a ceramic are acceptable for most applications and the problems normally encountered with mismatches in the coefficients of expansion are minimal. Undue experimentation is not believed to be necessary to optimize the desired properties by adjusting alloy composition and preparation.

Understanding the reasons for the formation of the articles described herein from the alloys described is incomplete at the present time. It is postulated that the advantageous properties achieved, according to the practice of the present invention are achieved by the relatively rapid transport of dissolved oxygen into the binary alloy of titanium and zirconium by its solution into the third alloying metal constituent which is present at the grain boundaries of the binary alloy constituents. Such a mechanism would help to explain why the ceramic layer obtained at relatively low temperatures remains monolithic and adherent rather than forming oxides simply as a surface phenomenon as previously done, which could produce scales which are easily dislodged if the oxidation were performed as described herein. Alloying materials which have high oxidizing agent transport properties should then be suitable for use in the practice of the present invention. In the practice of the present invention it has been discovered niobium, tantalum and vanadium provide both passivation of the ignition characteristics of the Ti—Zr binary alloy and dissolved oxygen transport for ceramic formation.

The following discussion is intended to advance further understandings of the invention while not being bound to any particular theory.

While the extensive work of W. Wyder and M. Hoch (The System Niobium-Titanium-Zirconium oxygen at 1500° C. Trans. Metallurg. Soc., AIME, Vol. 224, pp. 373–378, 1962) in constructing the Nb—Ti—Zr phase diagrams representing oxygen levels of 10, 20, 30, 40, 50 and 55 atomic % is recognized as a classical accomplishment, the fact that it represents only the isotherm at 1500° C. limits its utility in studying oxidation at the lower temperatures employed in the practice of the present invention.

A more relevant phase diagram is that of the Zr—Ti—Nb system at 570° C. published in 1968 by F. Ishida, (Ishida, F., T. Doi and M. K. Tada *Nippon Kinzoku* Gakkaishi, Vol. 32, No. 7, pp. 684–685, 1968) although one must always bear in mind the effects of oxygen on the system which may be estimated from the metal-oxygen binary phase diagrams.

Figure 21:
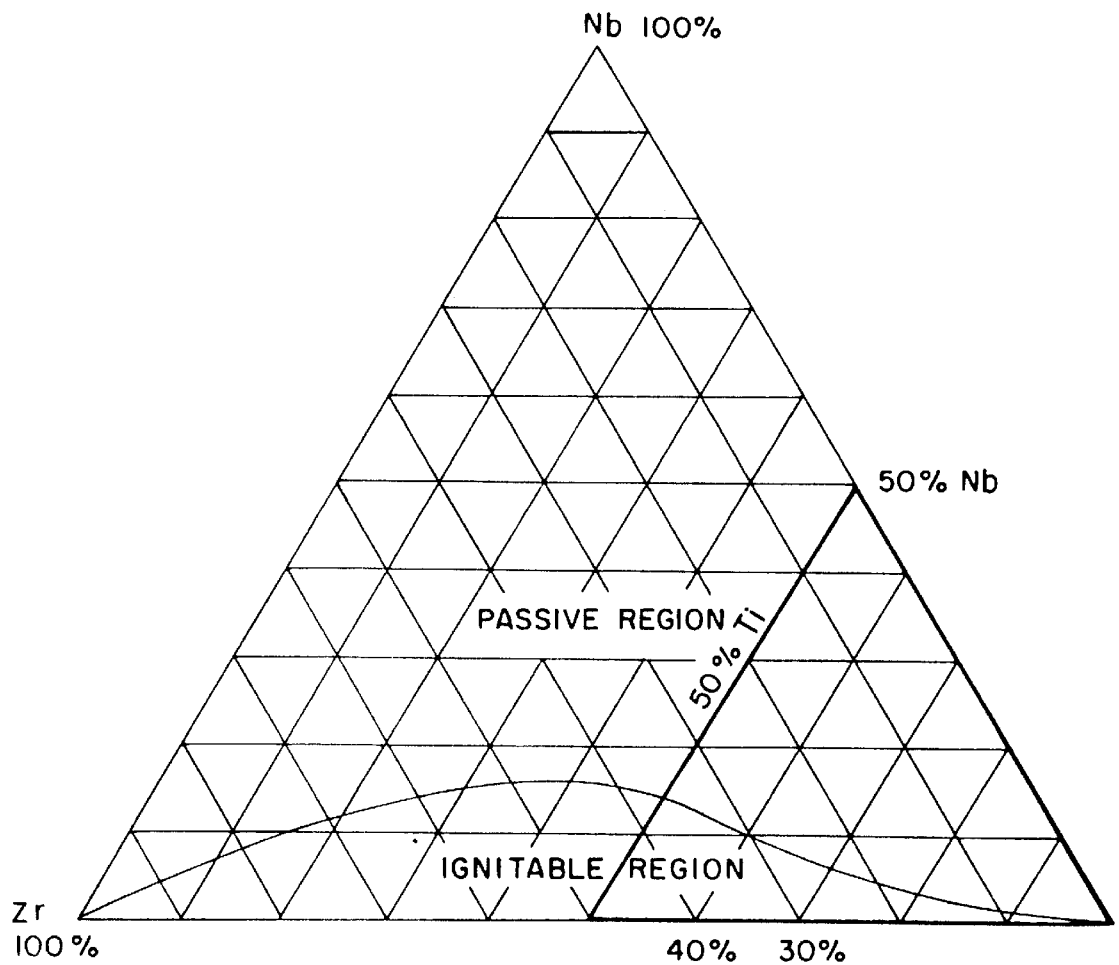
FIG. 21 is a ternary oxidation diagram for all alloys of Ti, Zr and Nb showing in atomic percent the entire passivation range produced by Nb additions.

The inventors herein have determined experimentally the boundary in the TiZrNb ternary system which separates alloys into "passive" and "ignitable" categories. The Ternary Oxidation diagram for Ti—Zr—Nb Alloys at 700° C. with the ignitable and passive regions identified is shown in FIG. 21. The titanium rich portion of that diagram is shown in larger scale in FIG. 4. The weight gain shown graphically for Alloys 7, 8, and 9 in FIG. 1 and Alloys 8 and 9 in FIGS. 2 and 3 can be related to the data contained herein. In attempting to account for the differences between various TiZrNb alloys, it was observed that transformations in the metallic phases do not explain observed differences in oxidation behavior. This observation, coupled with the realization that all such alloys owe their oxidation resistance to protective oxide surface films, could lead one to conclude that studies of the oxide phases are more appropriate toward understanding oxidation behavior. The works of Kofstad, P. *High Temperature Oxidation of Metals*, John Wiley and Sons, Inc., New York, 1966, and others present methods of identifying various mechanisms of oxidation based upon determining characteristic shapes of oxidation rate curves. An example of this approach is that of the oxidation kinetics of titanium at various temperatures. Referring to the general equation $w^n = kt$ (where w=weight gain per unit area, t=time, k=a constant), oxidation occurs at the following rates within indicated temperature regimes:

| | | |
|---|---|---|
| I: | 100–400° C. | logarithmic |
| II: | 400–600° C. | transition (log - parabolic or cubic) |
| III: | 600–1000° C. | parabolic |
| IV: | 1000–1100° C. | linear |

Phase I is dominated by oxide film formation, II by oxygen dissolution in which cubic-versus-parabolic behavior is determined by pre-existing oxygen gradients in the metal, III by a combination of oxygen dissolution and scale formation, and IV by loss of protective behavior.

In addition to reviewing empirical studies of oxidation kinetics, it is important to appreciate the large number of phases which may be observed in oxidation products of TiZrNb alloys. Although Zr in oxides is nearly always tetravalent, three allotropic forms of $ZrO_2$ are observed: monoclinic (at $\leq 949°$ C.), tetragonal (949°–1221° C.), and cubic (>1221° C.)$_{30}$. Titanium presents a much more extensive spectrum of oxides:

| Oxide | Structure |
|---|---|
| α-TiO | monoclinic |
| β-TiO | cubic |
| $Ti_2O_3$ | hexagonal |
| $Ti_3O_5$ | monoclinic |
| $TiO_2$ (anatase) | tetragonal |
| $TiO_2$ (rutile) | orthorhombic |
| $TiO_2$ (brookite) | hexagonal |

Niobium oxides are nearly as diverse as those of titanium:

| Oxide | Structure |
|---|---|
| NbO | cubic |
| $Nb_2O_3$ | |
| $NbO_2$ | tetragonal |
| $Nb_2O_5$ | orthorhomic |

Figure 5:
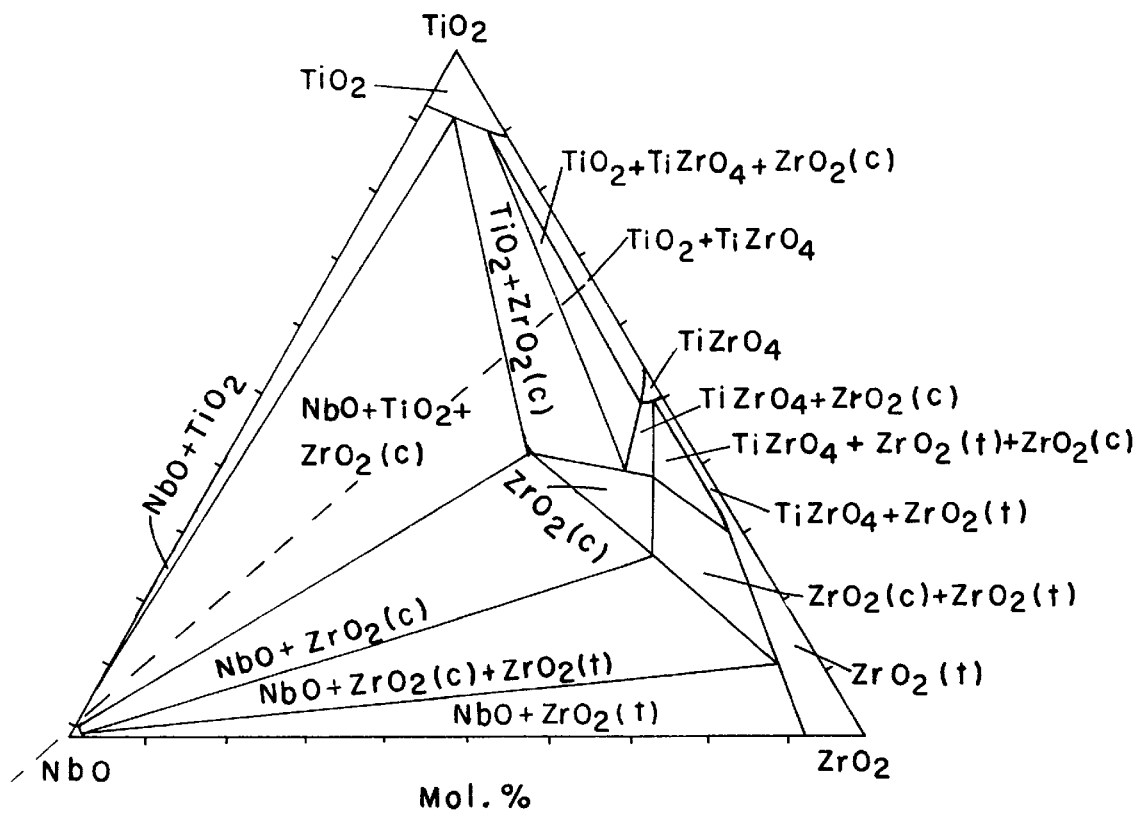
FIG. 5 is a phase diagram at 1500° C. of mixed titanium, zirconium and niobium oxides published by Levin, E. and H. McMurdie, Phase Diagrams for Ceramists, 1975 Supplement, p. 169 American Ceramic Society.

In understanding the possible phases which may be observed in TiZrNb oxidation products, one must not only consider the single oxides of each metal, but much more complex compounds formed in the quaternary system Ti—Zr—Nb—O shown in FIG. 5. (and more with description).

The following examples further describe the processes, compositions, and products encompassed within the scope of the present invention. In the examples it is demonstrated that under certain conditions the binary alloy of titanium and zirconium is passivated from undergoing combustion-like oxidation by the addition of niobium or tantalum, or vanadium (or mixtures thereof) in modest amounts.

EXAMPLE 1

A. Oxidation of TiZrNb Alloys at 600°–800° C.

Twenty vacuum-arc-melted alloy buttons (Table I) representing five different Nb concentrations (3.5, 5.7, 7.0, 10.5 and 14 at .%) at various Zr:Ti atomic ratios (2:1–1:3) were prepared for thermogravimetric studies of oxidation rate. Duplicate buttons were prepared and studied for five of the 15 different compositions.

For thermogravimetric evaluation, 400-g buttons of each alloy were sectioned and machined to yield specimens of approximately 10×18×18 mm. All buttons were given a vacuum heat treatment for one hour at 1500° C. and furnace-cooled to ensure alloy homogeneity. Each specimen was weighed to the nearest 0.1 mg and measured dimensionally to determine total surface area. Oxidation was effected by placing sets comprised of specimens of each alloy in an electric resistance furnace (air atmosphere) for times of 10, 20, and 30 minutes at temperatures of 600°, 650°, 700°, 750° and 800° C., respectively.

Visual observations of the specimens were made at approximately five-minute intervals in order to determine more accurate ignition times at particular furnace temperatures. Ignition was indicated by visible sparking and a distinct color change as the specimen temperature rapidly exceeded furnace temperature. During oxidation, samples were placed in random locations on a metal plate which rested on the bottom of the furnace and whose temperature was monitored by a thermocouple. Specimens were placed into 25 ml fireclay crucibles in order to contain spalling oxidation product which might otherwise contaminate neighboring specimens. Included in each furnace cycle were coupons (1.5×25×5–0 mm) of pure Zr, Hf, Ti, and Nb, which served as standards with known oxidation kinetics. Following oxidation, weight-gain values were determined in units of $mg/dm^2$, in accordance with customary corrosion rating convention.

In an effort to obtain more data points by which to establish a boundary in the TiZrNb ternary system separating "passive" from "ignitable" alloys, six additional compositions were cast (Table II).

TABLE I

Chemical Composition

| | | Calculated Values | | | | | | Actual Analysis | | |
|---|---|---|---|---|---|---|---|---|---|---|
| Alloy | Zr:Ti | Atomic % | | | Weight % | | | Weight % | | |
| No. | At. Ratio | Zr | Ti | Nb | Zr | Ti | Nb | Zr | Ti | Nb |
| 1 | 2:1 | 64.5 | 32 | 3.5 | 78 | 17.7 | 4.3 | 77.3 | 18.5 | 4.26 |
| 2A | 15:1 | 48.3 | 48.2 | 3.5 | 62.6 | 32.8 | 4.6 | 62.8 | 32.8 | 4.35 |
| 2B | 1:1 | 48.3 | 48.2 | 3.5 | 62.6 | 32.8 | 4.6 | 62.6 | 33.0 | 4.43 |
| 3 | 1:2 | 32 | 64.5 | 3.5 | 46.1 | 48.8 | 5.1 | 46.4 | 48.7 | 4.90 |
| 4 | 2:1 | 62 | 31 | 7 | 72.6 | 19.1 | 8.3 | 72.7 | 19.6 | 7.76 |
| 5 | 1:1 | 46.5 | 46.5 | 7 | 59.6 | 31.3 | 9.1 | 59.6 | 31.5 | 8.86 |
| 6 | 110:1.5 | 37 | 56 | 7 | 50.3 | 40 | 9.7 | 50.6 | 40.3 | 9.15 |
| 7 | 1:2 | 31 | 62 | 7 | 43.9 | 46.1 | 10.0 | 43.6 | 47.0 | 9.42 |
| 8 | 1:2.5 | 26.5 | 66.5 | 7 | 38.7 | 50.9 | 10.4 | 37.3 | 52.9 | 9.77 |
| 9 | 1:3 | 23.2 | 69.8 | 7 | 34.6 | 54.7 | 10.7 | 34.8 | 55.1 | 10.1 |
| 10A | 2:1 | 59.7 | 29.8 | 10.5 | 69.4 | 18.2 | 12.4 | 69.7 | 18.8 | 11.4 |
| 10B | 125:1 | 59.7 | 29.8 | 10.5 | 69.4 | 18.2 | 12.4 | 69.8 | 18.8 | 11.5 |
| 11 | 1:1 | 44.8 | 44.7 | 10.5 | 56.7 | 29.7 | 13.6 | 57.4 | 30.1 | 12.5 |
| 12A | 1:2 | 29.8 | 59.7 | 10.5 | 41.5 | 43.6 | 14.9 | 42.6 | 43.4 | 14.0 |
| 12B | 1:2 | 29.8 | 59.7 | 10.5 | 41.5 | 43.6 | 14.9 | 42.5 | 43.5 | 14.0 |
| 13 | 1:1 | 43 | 43 | 14 | 53.9 | 28.3 | 17.8 | 54.7 | 28.7 | 16.6 |
| 14A | 220:1 | 64.5 | 29.8 | 5.7 | 75 | 18.2 | 6.8 | 75.4 | 18.2 | 6.39 |
| 14B | 2:1 | 64.5 | 29.8 | 5.7 | 75 | 18.2 | 6.8 | 74.7 | 19.0 | 6.36 |
| 15A | 1:2 | 29.8 | 64.5 | 5.7 | 42.9 | 48.8 | 8.3 | 44.2 | 47.9 | 7.89 |
| 15B | 1:2 | 29.8 | 64.5 | 5.7 | 42.9 | 48.8 | 8.3 | 44.2 | 48.6 | 8.19 |

TABLE II

Additional Alloys

| Alloy No. | Zr:Ti | Atomic % | | | Weight % | | |
|---|---|---|---|---|---|---|---|
| | | Zr | Ti | Nb | Zr | Ti | Nb |
| 16 | 1:5.44 | 14.8 | 80.5 | 4.7 | 23.9 | 68.3 | 7.8 |
| 17 | 1:5.45 | 14.3 | 77.9 | 7.8 | 22.7 | 64.8 | 12.5 |
| 18  5 | 1:3.62 | 19.6 | 71.0 | 9.4 | 29.5 | 56.1 | 14.4 |
| 19 | 1:1.86 | 31.2 | 58.0 | 10.8 | 42.5 | 41.5 | 15.0 |
| 20 | 1.18:1 | 47.8 | 40.6 | 11.6 | 53.1 | 23.7 | 13.2 |
| 21 | 1.38:1 | 54.0 | 39.1 | 6.9 | 66.2 | 25.2 | 8.6 |

Specimens of these compositions were tested only for ignitability at 650°, 700°, and 800° C. No time-dependent weight gain data were taken for these specimens.

B. Oxidation of TiZrNb Alloys at 1200°–1500° C.

Additional specimens of the experimental alloys were oxidized in air for 1.0 hr at 1200° C. This treatment was sufficient to obtain heavy oxide layers on even the most passive alloys. The oxides were evaluated by X-ray diffraction, metallography, and electron microprobe.

C. Evaluation of a Ti35Zr10Nb (wt. %) Developmental Ingot

A triple-melted, 4-inch-diameter (101.6 mm) version of Alloy No. 9 (Table I) was produced from Ti sponge, Zr sponge and Nb46Ti (wt. %) turnings by conventional consumable electrode vacuum arc melting methods. This alloy, had a chemical composition of 54.7Ti34.6Zr10.7Nb (wt. %), equivalent to 69.8Ti23.2Zr7Nb (atomic %). After removal of the shrink pipe and minor sidewall machining, the ingot measured 3.95" dia.×6.5" long and weighed 15.3 lb (100.3 mm×165.1-mm, 6.94 Kg). Forging at 800° C. was performed in accordance with the following schedule:

1) Upset 6.5" dimension to 4.5".
2) Square to 4" tk×6" wide.
3) Reheat 15 minutes at 800° C.
4) Reduce tk to 2".
5) Reheat 15 minutes at 800° C.
6) Finish to 1.375×5"×L.

Samples were cut from top and bottom of the slab for chemical analyses.

The forging was hot rolled at 800° C. (17% reduction per pass) without reheating to 0.510" (12.95 mm) thick and cut in half. Following descaling and chemical cleaning (HF/HNO$_3$), a portion of the plate was again heated to 800° C. and rerolled to 0.260" (6.6 mm), again using 17% reductions without reheating. Samples representing the rolled condition were annealed for 1.0 hr at 800° C. and the remainder of the material was then solution-treated for 60 minutes at 850° C., followed by water quenching. The quenched plate was then sheared into specimens for precipitation hardening studies at 500° C. for times of 15, 30, 60, 120 and 180 minutes. Specimens representing the as-quenched and 120-minute aged conditions were submitted for tensile testing.

Young's modulus was determined for specimens of the as-rolled, as-quenched and variously-aged conditions. These measurements were obtained by a dynamic "impulse response analysis" (IRA) method. In this method, a specimen is supported in such a way as to allow free vibrational motion when a mechanical impulse is applied to it. The IRA instrument and accompanying software analyze the vibrational characteristics of the specimen and calculate elastic modulus. Although the method is capable of determining both flexural and torsional moduli, from which Poisson's ratio may be calculated, only flexural moduli were determined in the present studies. This method allows the same specimen to be non-destructively evaluated after various heat treatment operations in an expedient manner.

Additional samples of ¼" and ½" plate were oxidized under various conditions of temperature (500°–1500° C.) and time (1–40 hours). Metallographic and SEM evaluations of the oxides were performed.

Preliminary evaluations were conducted by machining cutting edges on a knife blank prepared from both as-quenched and precipitation-hardened plate, followed by various surface oxidation treatments in an attempt to determine the alloy's potential as a cutting implement. The knife blank was prepared by machining, heat treating and finishing of an existent knife blade design. This demonstration blade was produced using the following specific process:

1) Solution-treat ¼" plate for 60 min. at 850° C., water quench.
2) Precipitation harden for two hrs. at 500° C., air cool.
3) Descale, chemically clean.
4) Machine blade profile to uniform 0.160" thickness.
5) Grind contours and edge
6) Oxidize for 90 min. at 650° C. to a blue-black color.
7) Assemble into finished knife. This knife was tested in a qualitative manner by many cycles of cutting various materials, resharpening and refinishing, the latter being accomplished by a variety of methods, including heating to up to about 500° C. for one to two hours in a self-cleaning oven home appliance. This latter treatment being used to duplicate instructions given to a consumer when resharpening and rereacting a knife blade of this type at home.

D. Evaluation of Larger Ingot of the Alloy

A 9.0"-dia. (229 mm) ingot of approximately 110 lb was produced by triple vacuum-arc-melting in an analogous manner to that used for the previous 4"-dia. developmental casting. Forging to 2"×11" cross section was performed at 850° C., followed by annealing for 30 min. at 815° C. Hot rolling to thicknesses of 0.310" (7.9 mm), 0.270" (6.85 mm) and 0.180" (4.6 mm) was accomplished at 800° C., with 17% reductions per pass. These sizes were produced for experimental production of two different types of knife blades and a forged version of plier jaws. In addition to these wrought products, scrap material was set aside during fabrication for input material to an investment-cast version of the plier jaws. Resulting products were evaluated by metallography and tensile testing.

RESULTS

Oxidation of TiZrNb alloys at 600°–850° C.

Table I presents calculated and actual chemical composition of the initial set of 20 cast buttons.

Oxidation weight gains (mg/dm2) are presented in Table III for the initial 20 buttons, whereas only qualitative ratings for ignitability of the six additional compositions of Table II are presented in Table IV. Blank entries in Table III indicate that either catastrophic ignition of the sample occurred during the test, or that earlier cycles of lesser severity had resulted in ignition, eliminating the need for further evaluation.

Figure 2:
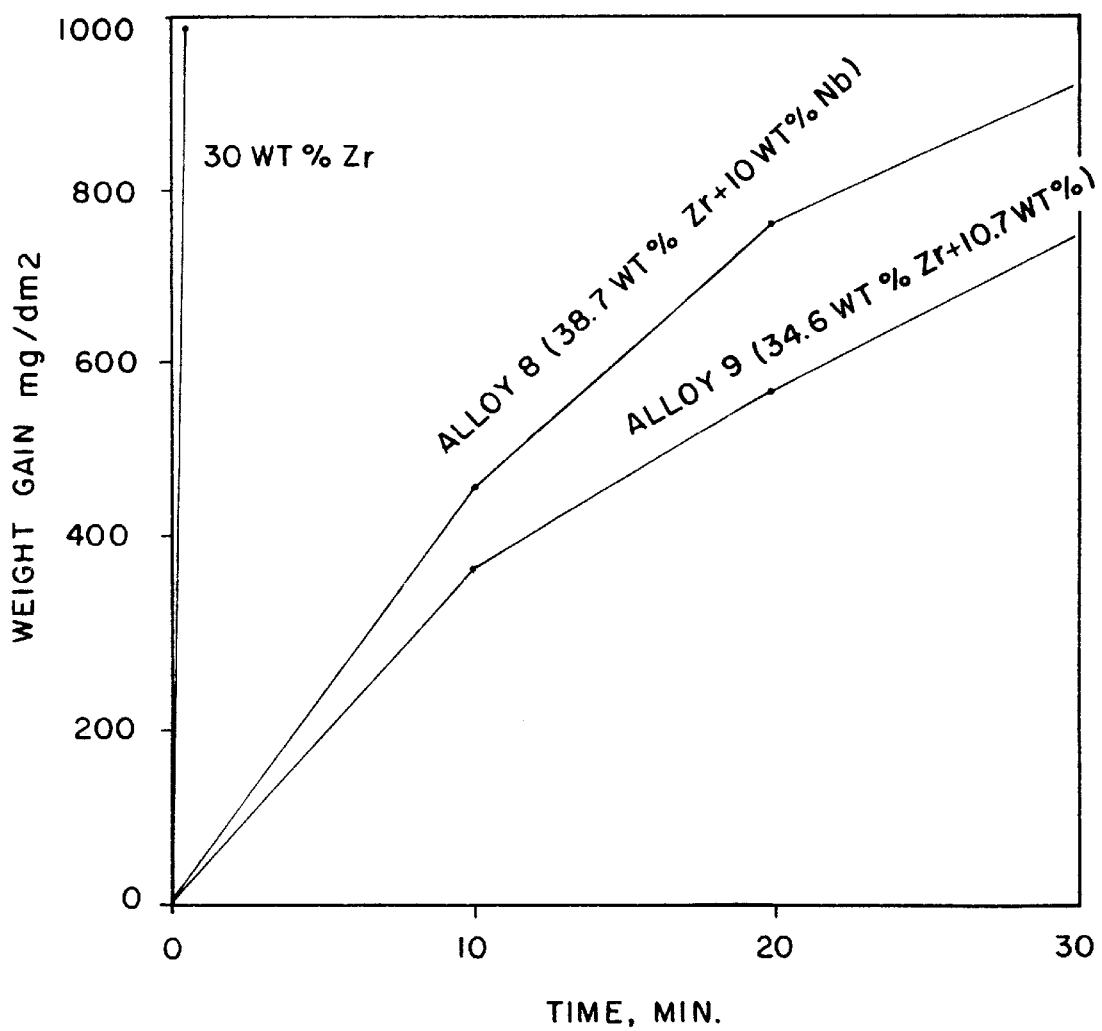
FIG. 2 is a graphical representation of some of the results reported in Table III of the weight gain of particular alloys at 800° C. as a function of time.
Figure 3:
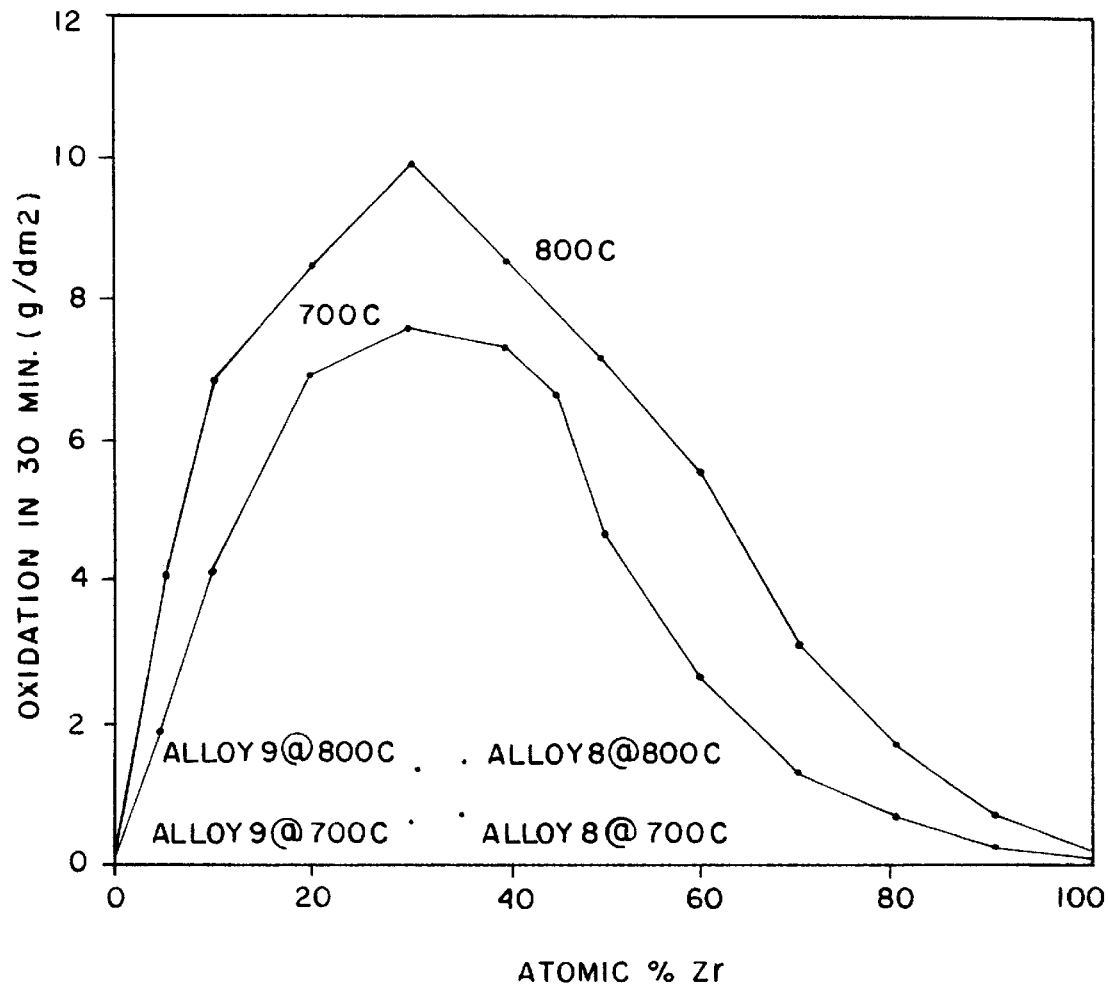
FIG. 3 is a graphical representation of the effect on the oxidation rate for Ti—Zr alloys of the addition of various amounts of niobium.

FIGS. 1 and 3 present comparisons between oxidation rates of Nb-containing alloys and corresponding binary TiZr alloys at 700° C. and 800° C.

Figure 4:
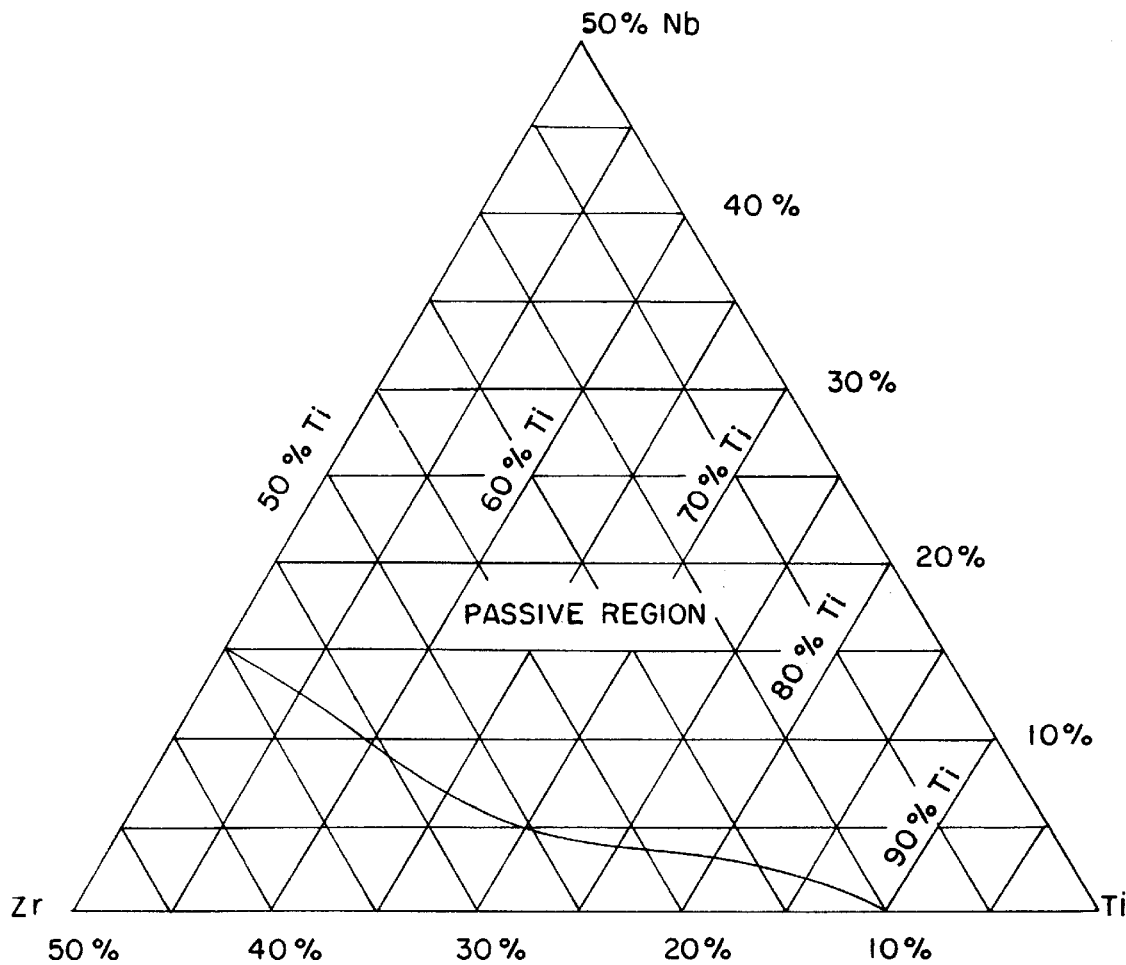
FIG. 4 is a Ternary Oxidation Diagram showing in atomic percentages the passivation range of titanium rich, zirconium alloys passivated by the addition of various amounts of niobium.

A ternary oxidation diagram is presented in FIG. 4, which separate Zr—Ti—Nb alloys into primary categories of "ignitable" and "passive" behavior. Data points obtained from the alloys identified in Tables I and II were used to generate the areas and boundary lines.

TABLE III

Oxidation Weight Gain Data (Units: mg/dm$^2$)

|  | 600 | | | 650 | | | 700 | | | 750 | | | 800 | | |
| --- | --- | --- | --- | --- | --- | --- | --- | --- | --- | --- | --- | --- | --- | --- | --- |
|  | 10 | 20 | 30 | 10 | 20 | 30 | 10 | 20 | 30 | 10 | 20 | 30 | 10 | 20 | 30 |
| 1 | 192 | 466 | 1029 | — | — | — | — | — | — | — | — | — | — | — | — |
| 2A | 127 | 288 | — | 196 | — | — | — | — | — | — | — | — | — | — | — |
| 2B | 125 | — | 314 | — | — | — | — | — | — | — | — | — | — | — | — |
| 3 | 34 | 138 | 25 | 94 | 200 | 303 | — | — | — | — | — | — | — | — | — |
| 4 | 112 | — | — | — | — | — | — | — | — | — | — | — | — | — | — |
| 5 | 78 | — | — | — | — | — | — | — | — | — | — | — | — | — | — |
| 6 | 55 | 219 | 241 | 168 | — | — | — | — | — | — | — | — | — | — | — |
| 7 | 25 | 88 | 104 | 105 | 242 | 428 | 279 | 508 | — | — | — | — | — | — | — |
| 8 | 18 | 58 | 66 | 39 | 89 | 136 | 100 | 216 | 354 | 341 | 552 | 791 | 466 | 771 | |
| 9 | 13 | 44 | 49 | 28 | 72 | 110 | 84 | 180 | 259 | 254 | 440 | 579 | 371 | 575 | |
| 10A | 102 | — | — | — | — | — | — | — | — | — | — | — | — | — | — |
| 10B | 136 | — | — | — | — | — | — | — | — | — | — | — | — | — | — |
| 11 | 108 | 215 | — | — | — | — | — | — | — | — | — | — | — | — | — |
| 12A | 61.7 | — | — | — | — | — | — | — | — | — | — | — | — | — | — |
| 12B | 24.8 | 123 | 75 | 84 | — | — | 161 | — | — | — | — | — | — | — | — |
| 13 | 40 | 178 | — | 117 | — | — | — | — | — | — | — | — | — | — | — |
| 14A | 149 | — | — | — | — | — | — | — | — | — | — | — | — | — | — |
| 14B | 159 | — | — | — | — | — | — | — | — | — | — | — | — | — | — |
| 15A | 32 | 111 | 80 | 68 | 202 | 305 | 201 | 495 | — | — | — | — | — | — | — |
| 15B | 31 | 133 | 70 | 41 | 216 | 306 | 237 | 656 | — | — | — | — | — | — | — |
| Zr | 4.3 | 16 | 21.7 | 17.4 | 41.1 | 51.1 | 44.6 | 65.1 | 78.3 | 74.8 | 94.6 | 120.9 | 107.3 | 144.5 | 179.4 |
| Hf | 0 | 0 | 1.2 | 0.8 | 4.3 | 4.3 | 4.7 | 6.2 | 11.2 | 0 | 12.0 | 15.5 | 14.0 | 20.2 | 26.0 |
| Ti | 0.4 | 1.6 | 0 | 0.8 | 4.3 | 4.3 | 4.2 | 6.2 | 8.9 | 12.8 | 16.7 | 23.6 | 20.2 | 31.4 | 47.3 |
| Nb | No data | 371 | 88 | 158 | 226 | 181 | 371 | 489 | 415 | 618 | 864 | 668 | 1062 | 1316 | |

TABLE IV

Oxidation Behavior of Additional Alloys

| Alloy | Ignition, Temp., °C. | Ignition Time, min. | Comments |
| --- | --- | --- | --- |
| 16 | None observed to 800° C. | — | Uniform oxidation |
| 17 | None observed to 800° C. | — | Uniform oxidation |
| 18 | None observed to 800° C. | — | Uniform oxidation |
| 19 | 800° C. (?) (specimen displayed elevated temperature but no spalling) | | |
| 20 | 650° C. | 15 | Combustion ceased after removal |
| 21 | 650° C. | 10 | Combustion continued after removal |

Biomedical Materials

The Ti—Zr alloys and their surface oxidation products exhibit many of the properties sought by the biomedical community for use in implanted prosthetic devices. Some of these properties are well known e.g. low toxicity, high-corrosion resistance, high strength, etc., It is desirable also to be able to match elastic modulus of implanted materials more closely to that of bone, and to provide porous surfaces to which tissue may bond by "ingrowth". At the present time, five metallic elements (Ti, Zr, Ta, Nb and Pt) have been demonstrated to have little or no adverse effects when implanted.

In reviewing the literature addressing metallic orthopedic implants, it is evident that in the past a wide variety of material and design selections have been utilized. Some examples involve the indiscriminate mixing of components such as screws and pins made of different alloys. This of course resulted in galvanic corrosion of the more anodic components as would be expected of dissimilar metals in the presence of an electrolyte (i.e., body fluids). Such corrosion is not only detrimental from the standpoint of reduced strength in the prosthesis, but also from release of corrosion products (metallic ions and inorganic debris) into the human body. In some cases, intimate contact of the dissimilar metals is not necessary for galvanic corrosion to occur. It is sufficient to merely locate such materials in the same local region of the body.

Ranking the suitability of various alloys for implant use by means of both in vitro and in vivo corrosion evaluations has shown that corrosion resistance increases in the order of 316L, Co—Cr alloys, and Ti6Al4V, all of which are presently widely utilized for implants. Another means of ranking materials, is to study electrochemical effects on biocompatibility, as determined by actual healing in human bone. When current densities in fast-reacting redox system, $K_4[Fe(CN)_6]_{/K_3}$—$[Fe(CN)_6]$ were measured, gold was highest, followed by stainless steel, Co—Cr, and Ti6Al4V. The same order was noted in observing the degree of disturbance in the initial bone healing process; i.e., gold interfered with healing to the greatest degree, while Ti6Al4V caused very little interference. The explanation which has been offered for these results is that surface oxides formed on some of these alloys are believed to serve to prevent the exchange of electrons and thereby suppress redox reactions at the implant surface. All of the alloys mentioned above owe their corrosion resistance to the presence of protective oxide films which serve as barriers to further diffusion of a variety of chemical species. There have been many successful techniques for imparting protective oxide films to such materials including Ti—Zr alloys. Destruction of these protective films by, for example, mechanical abrasion and the ease with which films reform are important factors in their selection for such uses.

It has been demonstrated that there is a transition from corrosion control to electron exchange control of polarization resistance during spontaneous passivation of film-forming alloys. An extremely complex series of transient conditions may therefore be encountered when abrasive wear and subsequent reformation of the passivating film are considered. Abrasion may not only degrade corrosion resistance but may also result in deposition of debris in joints. This is the primary reason that Co—Cr alloys are presently utilized for knee joint prostheses, whereas Ti6A+4V may be superior in hip joint replacements which do not involve such severe shear/abrasion stresses. Because of the poor resistance to "fretting wear" displayed by conventional Ti alloys, a demonstrable need exists for a titanium containing alloy which is capable of having formed thereon a protective oxide surface layer which is capable of resisting abrasive, fretting wear.

Referring to FIG. 21 and the photomicrographs, a typical Ti—Zr alloy containing more than about 10–20 wt % Zirconium will have the undesirable ignitable property described herein unless that rapid oxidation behavior is moderated with the addition of small amounts of niobium, tantalum or vanadium. These ignitable alloys have previously been unsuitable for many uses, in particular in the fabrication of metal prosthetic devices, and the study of their other properties has therefore been largely ignored.

While there are many schemes to provide passive oxide surfaces on the non-ignitable alloys containing Titanium and Zirconium only alloys containing Ti—Zr—Nb that contained less than about 20 wt % Zr have been reported. The surface oxides formed have been imported by molten salt baths and the like which results in a very thin layer to resist abrasion in use.

Figure 6:
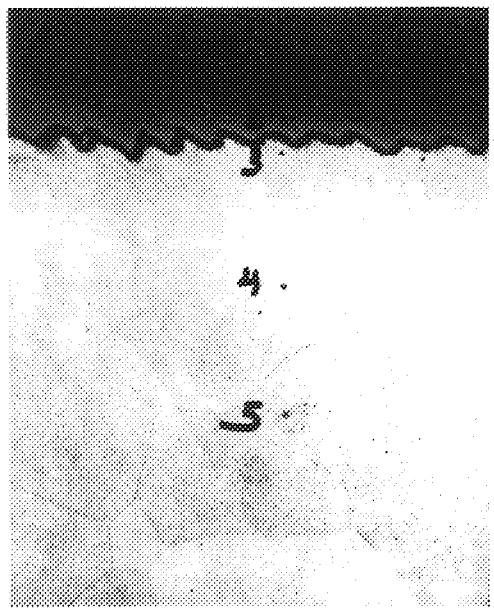
FIG. 6 is a photomicrograph of a passivated Ti—Zr—Nb alloy according to this invention that has been oxidized in air for 10 minutes at 750° C.
Figure 8:
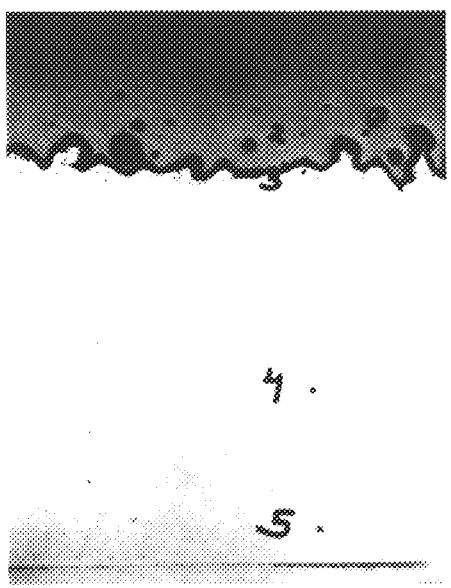
FIG. 8 is a photomicrograph of a passivated Ti—Zr—Nb alloy according to this invention that has been oxidized in air for 30 minutes at 750° C.
Figure 9:
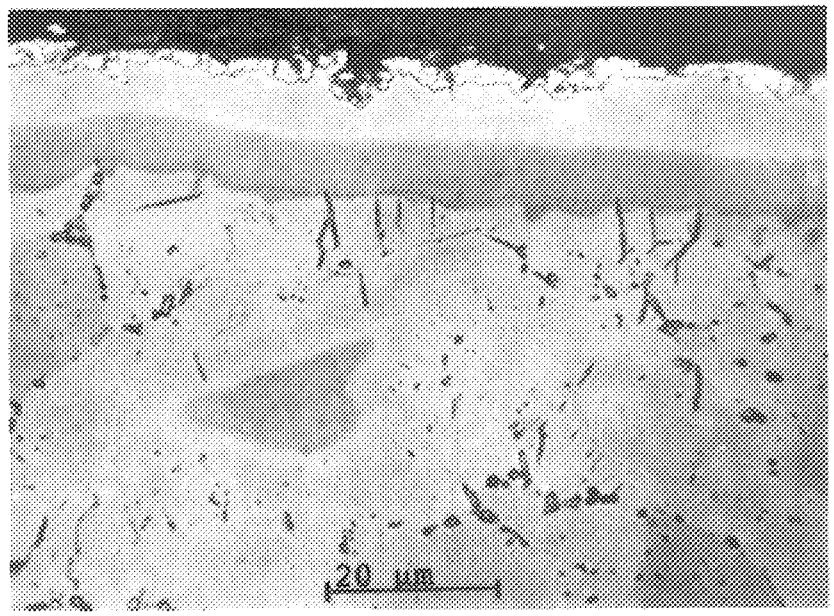
FIG. 9 is a photomicrograph of pure Zirconium nitrided for one hour at 1200° C.
Figure 10:
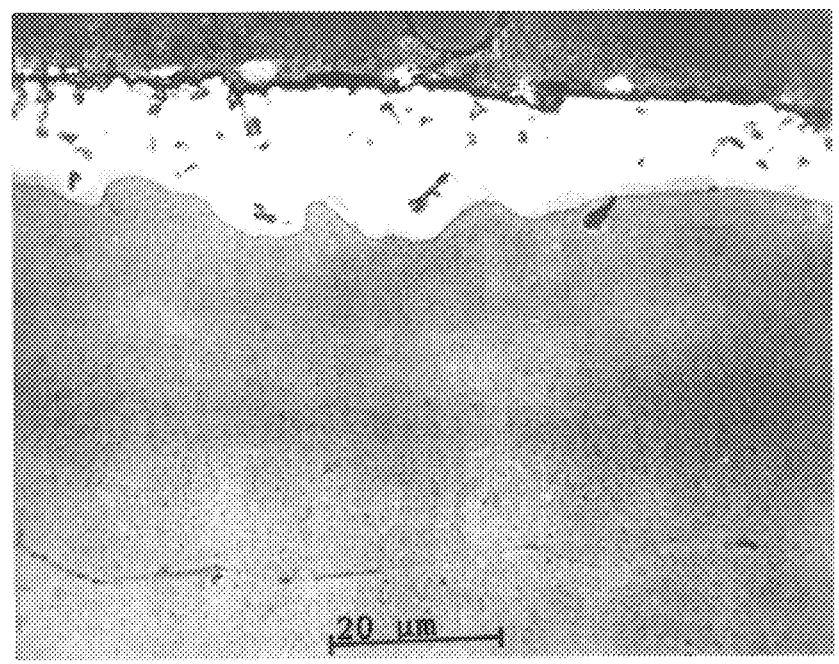
FIG. 10 is a photomicrograph of titanium nitrided for one hour at 1200° C.
Figure 11:
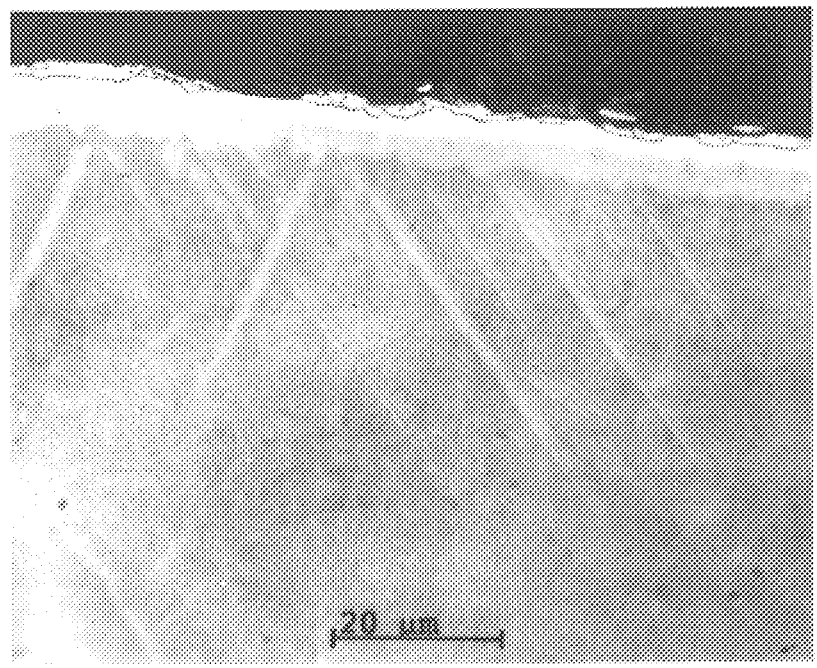
FIG. 11 is a photomicrograph of a passivated Ti—Zr—Nb alloy according to this invention that has been nitrided for one hour at 1200° C.
Figure 12:
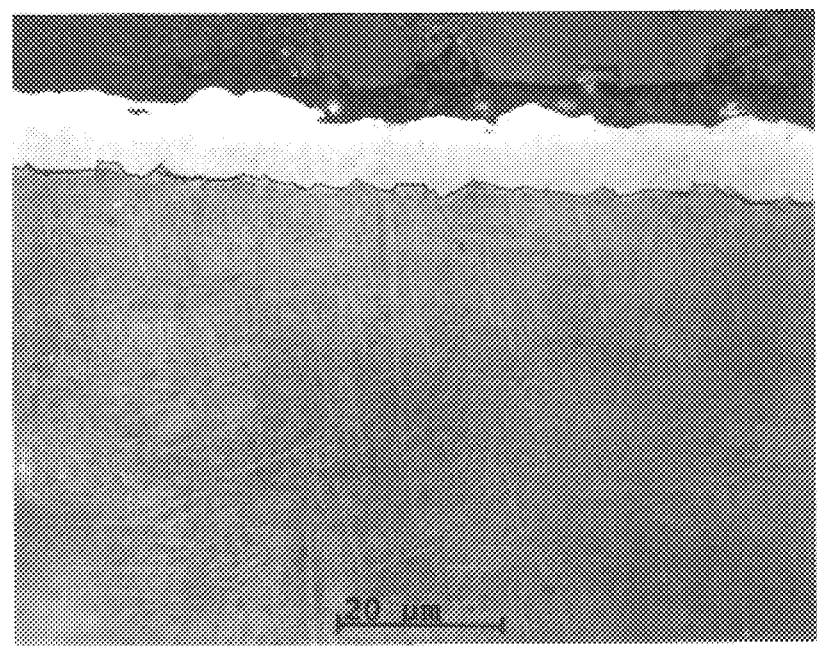
FIG. 12 is a photomicrograph of a passivated Ti—Zr—Nb alloy according to this invention that has been nitrided for six hours at 1200° C.

The exemplary TiZrNb alloy described herein i.e. 35 wt % Zr 10 wt % Nb when oxidized for short times at various temperatures in air, produces a thick monolithic adherent oxide layer in the surface of the metal. Fore example, FIG. 6 shows oxidation for 10 minutes at 750° C., FIG. 7, 20 minutes at 750° C. and FIG. 8, 30 minutes at 750° C. The resultant oxide surface layer shown in each photograph is dense and adherent. Other oxidation behavior was also studied. FIG. 9 shows a nitride layer on pure Zirconium formed after the 1 hour at 1200° C. FIG. 10 shows a nitride layer on pure Titanium formed after 1 hour at 1200° C. These two layers can be visually compared with a nitride layer on 35 Zr 10 Nb wt % formed after 1 hour at 1200° C. (FIG. 12).

An additional value is obtainable from the alloys and products of the present invention because of the low modulus of elasticity that can be achieved with these alloys. Low modulus materials are now preferred for the following reasons.

Because of problems in attaching prostheses to bone with adhesives, a trend has developed toward the use of cementless, interference fit methods.

Viewing the human femur from the front or rear, a significant curvature (concave downward) is noted as the bone deviates from the generally straight lower segment of the femur toward the hip socket. In a normal bone, the body's weight tends to flex this region so that the curvature increases as weight is shifted to that side of the body. The Young's elastic modulus of cortical bone is about 31 GPa (4.5 Mpsi), far below values for common engineering alloys-. When a relatively stiff prosthesis is inserted into the intramedullary canal of the femur, the curved region in question may become "shielded" from flexural stresses. As is true of other biological structures (e.g., muscles), the absence of stress and flexure may result in a form of atrophication. In the specific case of bone "shielding", the body resorbs and weakens the bone, which may ultimately cause loosening or fracture of the prosthetic stem. Attempts to design the prosthesis so that the curved region of the femur experiences increased stresses by increasing the length of the curved neck have created excessive moments at other points, causing fractures. A logical approach to this problem would appear to be to develop suitable alloys with lower elastic modulus values, while preserving adequate strength, corrosion resistance and other required attributes.

Significant reduction in bone resorption have been demonstrated in dogs and sheep with low modulus hip implants. Finite element analyses have also confirmed that healthy femurs are more closely simulated by low modulus materials. Strain gauge analyses have also confirmed this finding. In human patients, bone resorption, loosening, and the pain which has clearly been attributed to excessive prosthetic stiffness has been shown to be reduced in frequency and severity by using low modulus hips. Metallic materials are felt to be preferable to other materials, such as polymer composites, because of cost considerations and the poor wear resistance of these composites.

Titanium alloys recently promoted for medical prosthetics include Ti5Al2.5Fe, Ti6Al7Nb and Ti11.5Mo6Zr2Fe. The first two of these still have relatively high modulus (105–115 GPa versus 120 GPa for Ti6Al4V) and contain the potentially undesirable element aluminum. The second contains relatively high concentrations of Mo and Fe, both of which have been demonstrated to cause severe tissue reactions. The alloys of the present invention contains only biocompatible elements and are therefore more desirable.

As will be more fully described hereinafter, the partial or complete conversion at higher temperatures, of the alloys of the present invention into their corresponding oxides and mixed oxides in the form of a reaction formed ceramic can also be useful as materials for prosthetic devices due to the inert character of the ceramic, the various pore sizes obtainable that may promote tissue ingrowth and the physical properties of the underlying metal in the case of partial conversion—no para ceramics, etc.

Ceramics formed from the subject TiZrNb alloys will be of interest as replacements or reinforcements for bone and teeth. Various other approaches to obtain porous ceramic structures into which bone may grow to form stable interfaces have been evaluated. These include sintered powders, foamed ceramics, preferential etching to remove included phases, and calcining natural materials such as coral. It has been found that controlling pore size and uniformity is essential to obtain optimum properties in these materials. Bone ingrowth requires pore diameters of at least 100 $\mu$m in order for nourishment to be continuously supplied to living cell structures, while excessive porosity or unnecessarily large pore diameters tend to weaken the ceramic prosthesis. The homogeneous distributions of predicatable uniformly-sized grains and pores associated with oxides formed from the subject TiZrNb alloys makes them desirable for such medical use.

Materials for Cutlery

Although wear resistance may be a primary consideration in selecting materials for cutlery implements, other properties such as fracture toughness, strength, and elastic modulus are also important. The poor corrosion resistance of plain carbon and low alloy steels resulted in large commercial markets for a martensitic class of stainless steels which is generally described by the relationship % Cr–(17X%C) <12.5. These alloys are capable of transforming from austenite to martensite upon quenching to yield relatively high hardness (50–55 $R_c$), whereas alloys in which % Cr–(17–X%C)>12.5 are strictly ferritic and are therefore not hardenable.

Recent interest in reducing weight in cutlery items has resulted in evaluation of titanium-based alloys. There are also special applications in which increased corrosion resistance in seawater and other chemical environments make titanium a potentially desirable material. Certain military applications require materials which are non-magnetic and low in surface reflectivity, or which do not display ductile-to-brittle transitions at low temperature. Still, other applications require high impact resistance or low elastic modulus to increase flexibility in such implements as fileting knives.

Although many of these desired properties may be provided by conventional titanium alloys such as Ti6Al4V, adequate hardness for cutting edges is difficult and expensive to obtain, often involving surface diffusion processes conducted for long times at high temperatures and in special environments such as autoclaves. Furthermore, the hard surface films (e.g., oxides, nitrides, carbides, borides) are impossible for the consumer to repair when resharpening becomes necessary. The oxidation characteristics of the subject TiZrNb alloys offers a potential solution to these problems.

It should be noted that many considerations applicable to consumer goods such as high-volume cutlery are non-technical in nature. A sportsman, for example, may prefer a softer knife which is easily sharpened to one which will "hold an edge" longer, while a housewife may prefer a kitchen knife which is not overly sharp and which does not need frequent sharpening.

Figure 13:
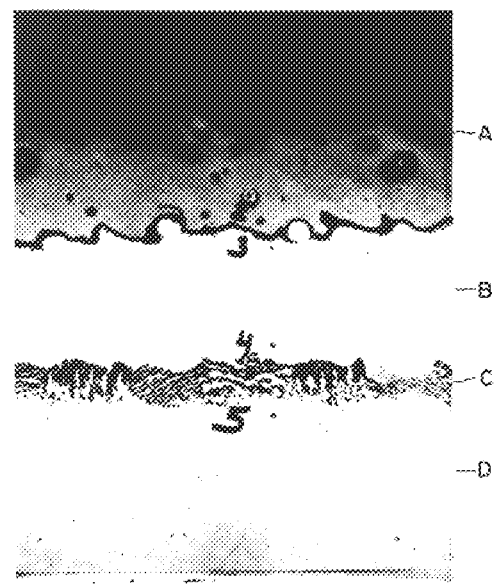
FIG. 13 is a photomicrograph of a passivated Ti—Zr—Nb alloy according to this invention which has been oxidized in air for 10 minutes at 800° C.

The morphology of the transformation of the Ti—Zr alloys which have been rendered non-ignitable according to this invention, into ceramic oxides is complex and not easily described. Referring again to the photomicrographs, FIG. 13 shows a sample of the typically examined 35Zr10Nb alloy oxidized in air for 10 minutes at 800° C. This is a temperature only slightly higher than the 750° C. results shown in FIGS. 6–8 for the same time. The oxide layer is shown at A, B is an area of alph-stabilized metal c is an area of mixed phases and D is the relatively unaffected metal alloy.

Figure 14:
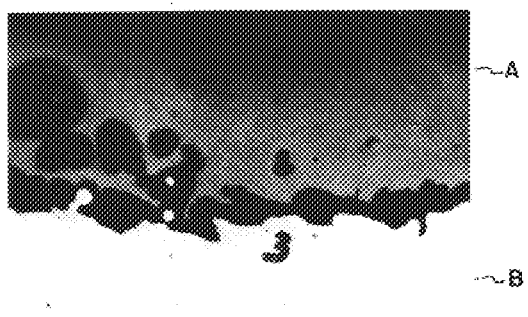
FIG. 14 is a photomicrograph of a passivated Ti—Zr—Nb alloy according to this invention which has been oxidized in air for 30 minutes at 800° C.
Figure 14:
Figure 15:
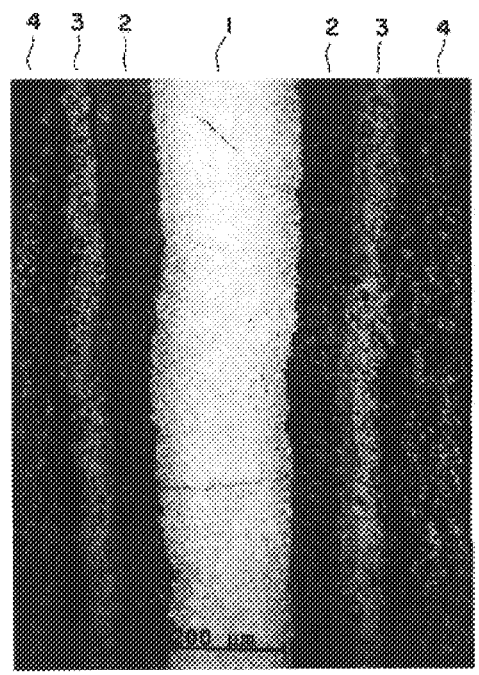
FIG. 15 is a photomicrograph of a thin metal section of a passivated Ti—Zr—Nb alloy according to this invention which has been oxidized in air at 1300° C.
Figure 19:
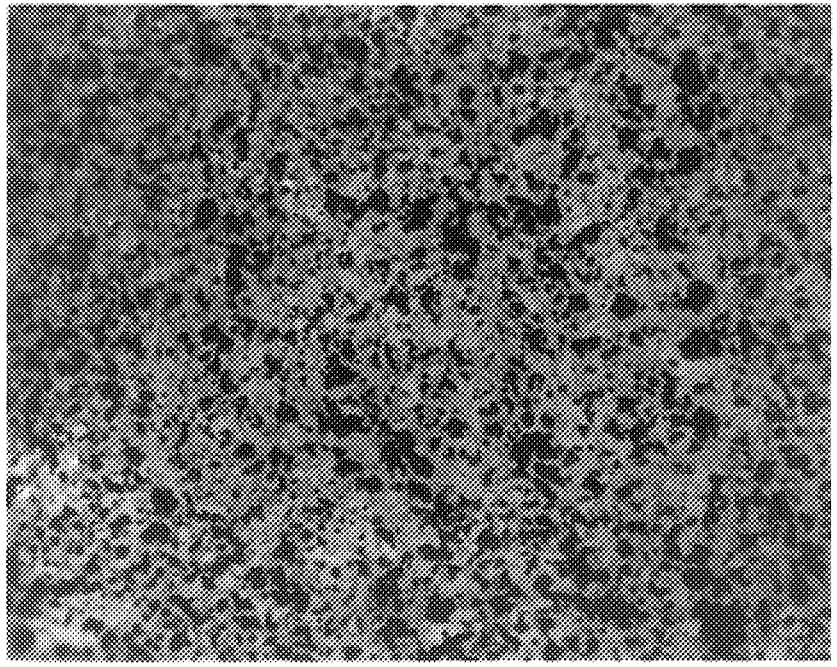
FIG. 19 is a 200 power photomicrograph of a ceramic formed according to the present invention at 1400° C.
Figure 20:
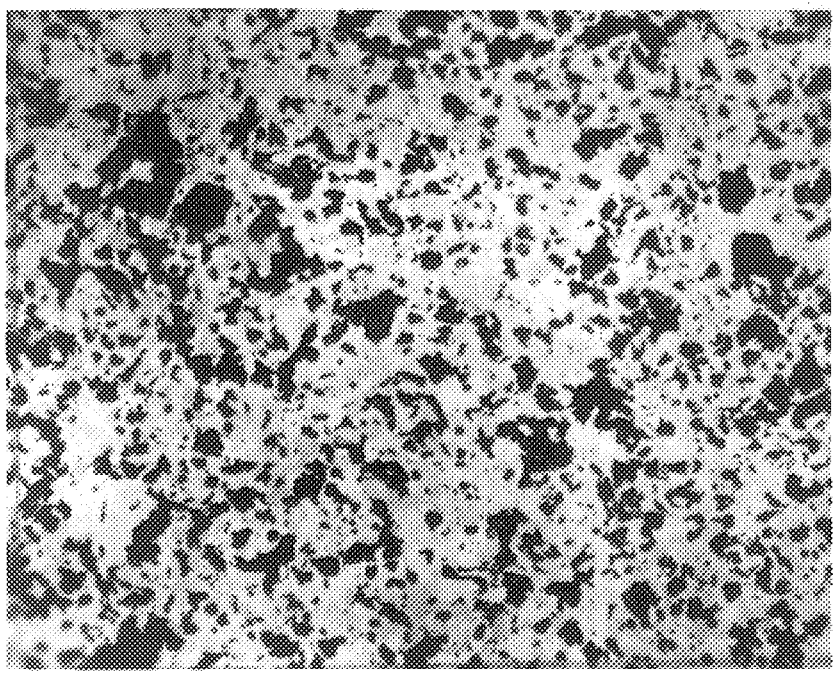
FIG. 20 is a 200 power photomicrograph of a ceramic formed according to the present invention at 1500° C.

Referring to FIG. 14, the same metal alloy is shown after oxidation in air for 30 minutes at 800° C. The oxide layer A is still visually well characterized while the alph-stabilized layer is larger and the mixed phase area is larger and less defined. In FIG. 15, a sample of 35Zr10Nb was oxidized in air at 1300° C. A much more complex picture of the conversion process is developed here. The metal substrate 1 originally was nearly as thick as the resultant oxide covered structure. The first layer of oxide obtaining material remains rich in niobium and is believed to be comprised of several oxide or suboxide species. The next layer 3 moving outward from the metal represents a transformation zone where conversion to the final oxide specie found in the outer surface 4 is taking place. Pores are being formed in layer 4 possibly as a result of this conversion process and larger pores form where the conversion is carried out at higher temperatures. FIG. 19 and FIG. 20 show respectively under 200 power magnification that the dark areas (pores) are smaller where the temperature of formation was 1400° C. (FIG. 19) than the larger pores formed at 1500° C. (FIG. 20). This ability to form uniformly distributed pores and to control the pore size by adjusting the temperature of the ceramic oxide formation while maintaining nearly constant pore volume percent porosity, can be useful in the fabrication of many articles including catalyst supports and the like where pore sizes is important to the intended performance of the finished article.

Figure 7:
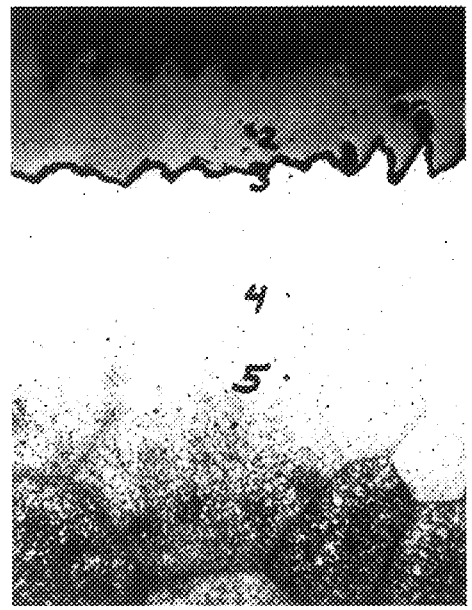
FIG. 7 is a photomicrograph of a passivated Ti—Zr—Nb alloy according to this invention that has been oxidized in air for 20 minutes at 750° C.
Figure 16:
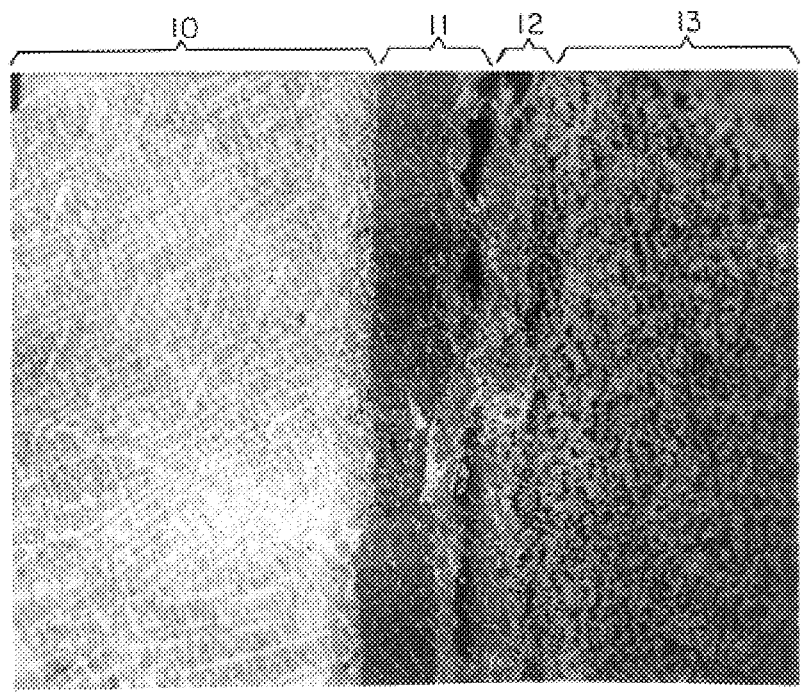
FIG. 16 is a photomicrograph of an alloy of the present invention oxidized in air at 1200° C. for 24 hours.
Figure 17:
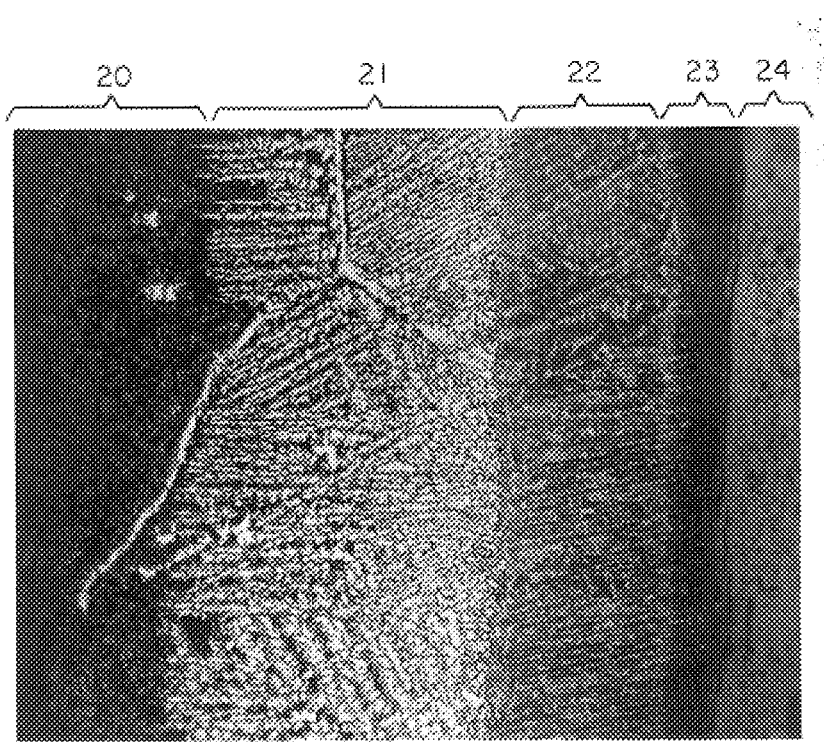
FIG. 17 is a photomicrograph of an alloy of the present invention oxidized in air at 1000° C. for 39 hours.

FIGS. 16 and 17 visually show that the adjustment of both time and temperature can be critical to different results being obtained in the final oxidized product. While oxide layer formation such as shown in FIGS. 6–8 can be achieved at relatively low temperatures and only short times, modestly higher temperatures and longer times produce radically different phenomenon. In FIG. 16 the metal substrate 10 was subjected to oxidation at 1000° C. for 39 hours. The 200 power photomicrograph shows the metal 10 with two visually identifiable intermediate zones or areas 11, and 12 underlying the final oxide 13.

In FIG. 17 the metallic substrate has at least three visually identifiable zones 21, 22 and 23, underlying the final oxide layer 24. Zone 21 appears to be a metallic zone with internal and grain boundary oxidation. FIG. 17 is a 200 power photograph of a 35Zr10Nb sample oxidized at 1000° C. for 39 hours.

Figure 18:
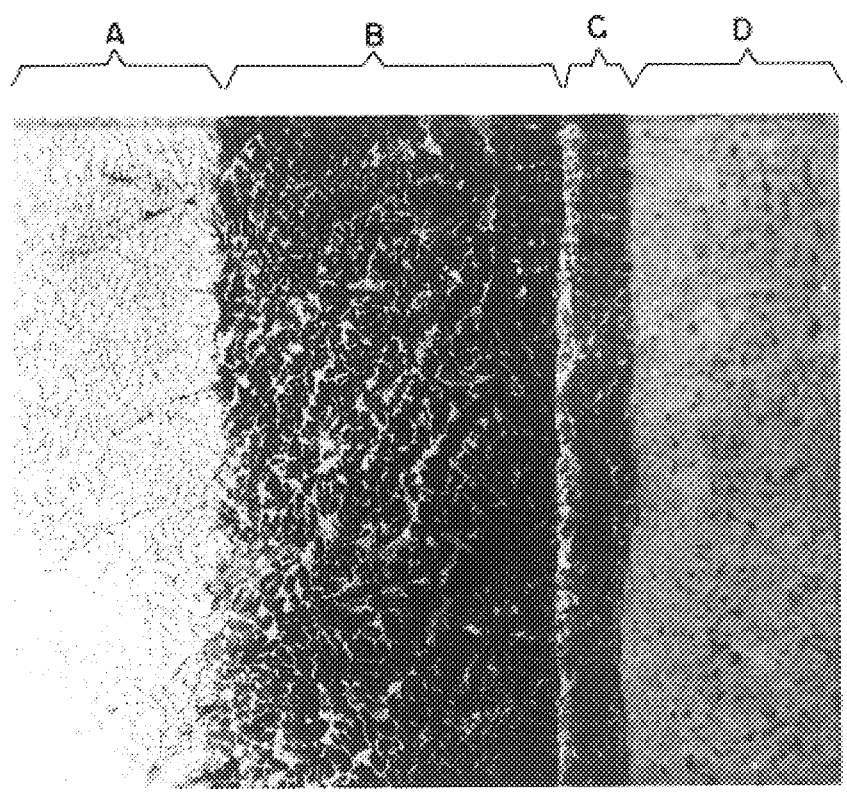
FIG. 18 is a photomicrograph of an alloy of the present invention oxidized in air at 1100° C. for 64 hours.

FIG. 18 is yet another example of the possible variations in the morphology of formation of the ceramic described herein. The 35 Zr10Nb alloy was oxidized in air for 64 hours at 1100° C. The 200 power photomicrograph clearly shows a metallic zone A, a metallic zone B and intermediate zone C and the surface oxide D.

Referring to FIG. 5 a very complex spectrum of possible oxide species are possibly formed during the ceramic conversion process.

The present studies of oxides formed at 1400°–1500° C. confirm the presence of $TiO_2$ (rutile form) which contains an appreciable amount of Nb, and a Zr-rich phase (probably $TiZrO_4$) which contains only a trace of Nb. The moderated oxidation rate of 35Zr10Nb may therefore be attributable to some ability of Nb to prevent interactions between the Zr-rich and Ti-rich phases which could otherwise lower the monoclinic <— —> tetragonal zirconia transformation temperature.

As previously described, tantalum and vanadium have been successfully substituted in the alloy of the present invention for the niobium, likewise the nitridation of the alloys reacts generally similarly and produces results similar to the air oxidation described herein.

This invention has been described with respect to its preferred embodiments and contemplated utility. Variations can be made without undue experimentation by those skilled in the art with the expected results being obtained without departing from the spirit and scope of the invention described in the appended claims as interpreted in view of the applicable prior art.

We claim:

1. A method of making a mixed metal oxide-containing ceramic product from a metal alloy consisting essentially of the steps of providing a metal alloy containing less than 90 atomic percent titanium and at least about 14 atomic percent of at least one of zirconium and hafnium and at least one of niobium, tantalum and vanadium, said total of niobium, tantalum and vanadium being present in said alloy in proportions of at least about 7 atomic percent to passivate the alloy and prevent the alloy from igniting and undergoing combustion when heated in air at atmospheric pressure to a temperature of from about 500° C. to 800° C., heating the alloy provided in air at atmospheric pressure and at a temperature of from about 800° C. to about 1500° C., which is equal to or above the ignition temperature of the alloy without the presence of Ni, Ta, or V, and for a time sufficient to form a ceramic product wherein said ceramic material contains mixed metal oxidation products that are adherent and monolithic.

2. The method of claim 1 wherein the alloy provided contain titanium, zirconium and niobium in the proportions in atomic percentages defined by the region of the ternary oxidation diagram of FIG. 21 identified as the passive region.

3. The method of claim 1 wherein the alloy provided contain titanium, zirconium and niobium in the proportions in atomic percentages defined by the region of the ternary oxidation diagram of FIG. 4 identified as the passive region.

4. The method of claim 1 wherein the titanium alloy provided contains about a 23 atomic percent (35% by weight) zirconium and about 7 atomic percent (10% by weight) niobium.

* * * * *